United States Patent [19]
Bender et al.

[11] Patent Number: 5,415,874
[45] Date of Patent: May 16, 1995

[54] NATURAL KILLER CELL LINES AND CLONES WITH ANTIGEN SPECIFICITY

[75] Inventors: Jeffrey R. Bender, Orange, Conn.; Ruggero Pardi, Milan, Italy; Edgar G. Engleman, Atherton, Calif.

[73] Assignee: The Board of Trustees of the Leland Stanford Junior University, Stanford, Calif.

[21] Appl. No.: 429,353

[22] Filed: Oct. 31, 1989

[51] Int. Cl.[6] .............. A61K 39/00; A61K 35/14; C12N 5/00; C07K 3/00
[52] U.S. Cl. .............. 424/520; 424/93.71; 435/240.1; 435/240.2; 435/240.21; 435/7.21; 435/7.24; 435/723; 435/29; 435/34
[58] Field of Search .............. 424/85.8, 520; 530/387; 435/240.1, 240.2, 240.21

[56] References Cited

U.S. PATENT DOCUMENTS 5,028,424 7/1991 Evans .................. 424/85.8

OTHER PUBLICATIONS

Bender et al. (1987) J. Clin. Invest. 79: 1679–1688.
Krensky, A. M., et al., Clin. Immunol. Rev. 4(1), 95–138 (1985).
Hercend, T., et al., Immunol. Today 9(10) 291–295 (1988).
Rosenberg, S., J. Natl. Cancer Inst. 75(4) 595–603 (1985).
Grimm, E. A., J. Exp. med. 155 1823–1841 (1982).
Pardi, R., et al., J. Immunol. 139(8) 2585–2592 (1987).
Bender, J. R., et al., J. Clin. Invest. 79 1679–1688 (1987).
Ciccone, E., et al., J. Exp. Med 168 2403–2408 (1988).
Ortaldo, J. R., et al., J. Immunol. 133(2) 779–783 (1884).

*Primary Examiner*—Robert J. Hill, Jr.
*Assistant Examiner*—Gian P. Wang
*Attorney, Agent, or Firm*—Gary R. Fabian; Peter J. Dehlinger

[57] ABSTRACT

Lymphocytes of NK phenotype were cultured with stimulator cell lines in the presence of growth factor containing medium. The resulting lines and clones derived from these lines expressed CD16 and/or Leu 19, but lacked detectable CD3 or T cell receptor γ/δ complexes on the cell surface. In addition to displaying potent cytolytic activity against K562 erythroleukemia cells (a classical NK target), the vast majority of these lines and clones lysed their specific stimulator cell lines to a significantly greater extent than irrelevant cell lines. These results indicate that some CD3− lymphocytes, phenotypically indistinguishable from NK cells, can recognize and lyse allogeneic targets in a specific manner.

14 Claims, 13 Drawing Sheets

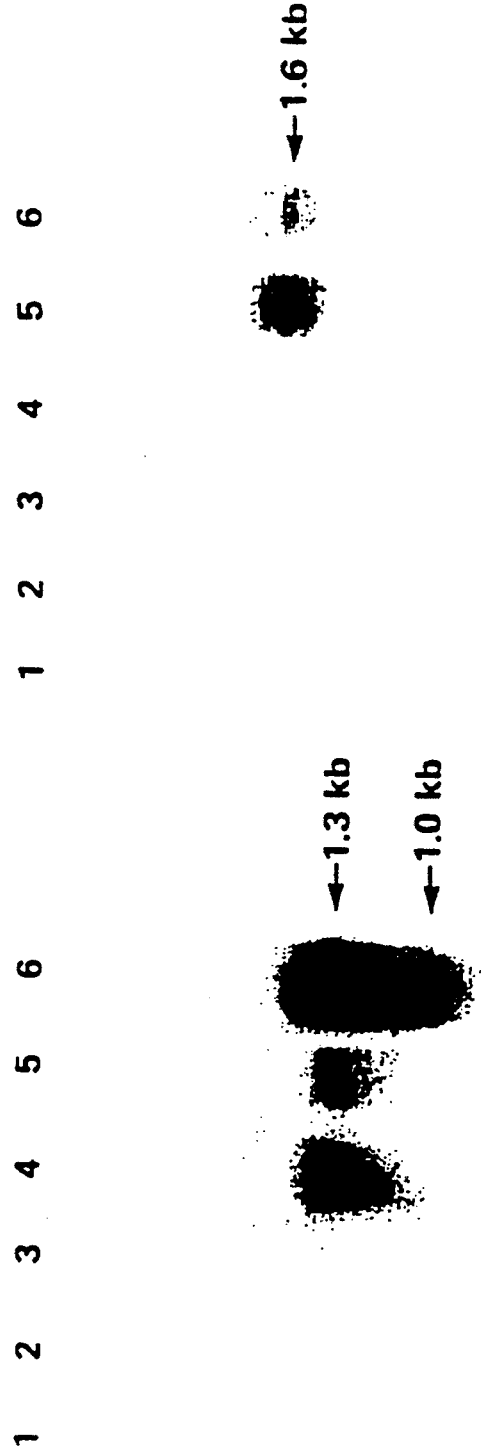

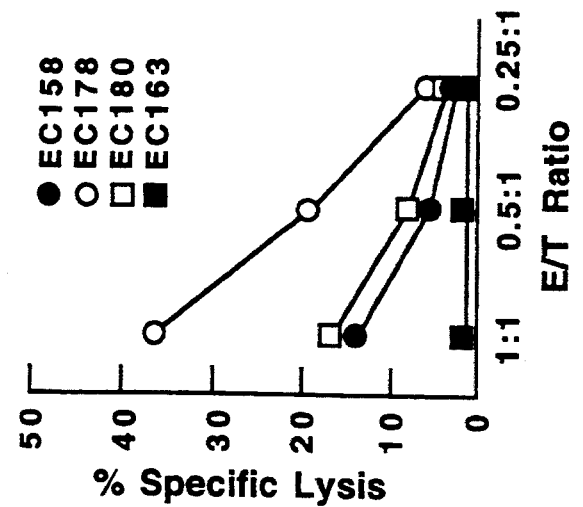
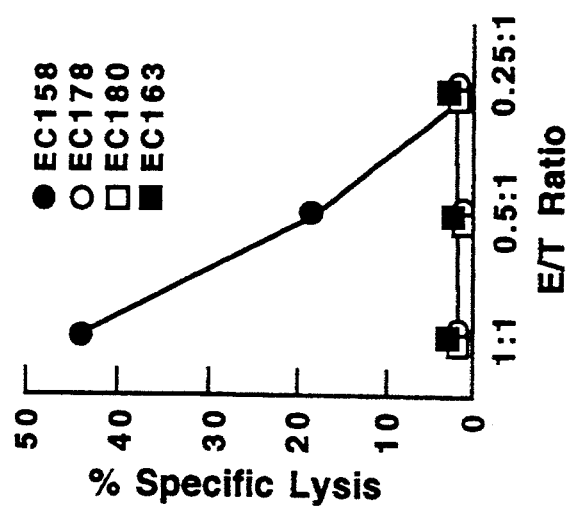
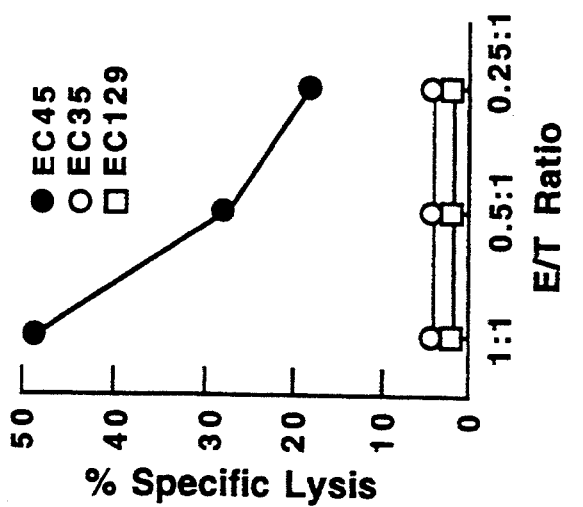
Fig. 3A
Fig. 3B
Fig. 3C

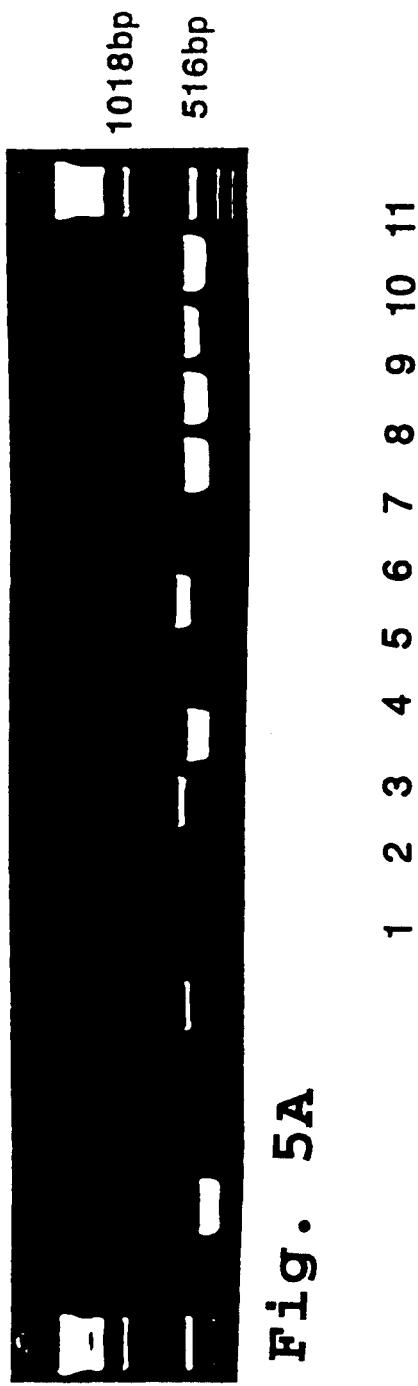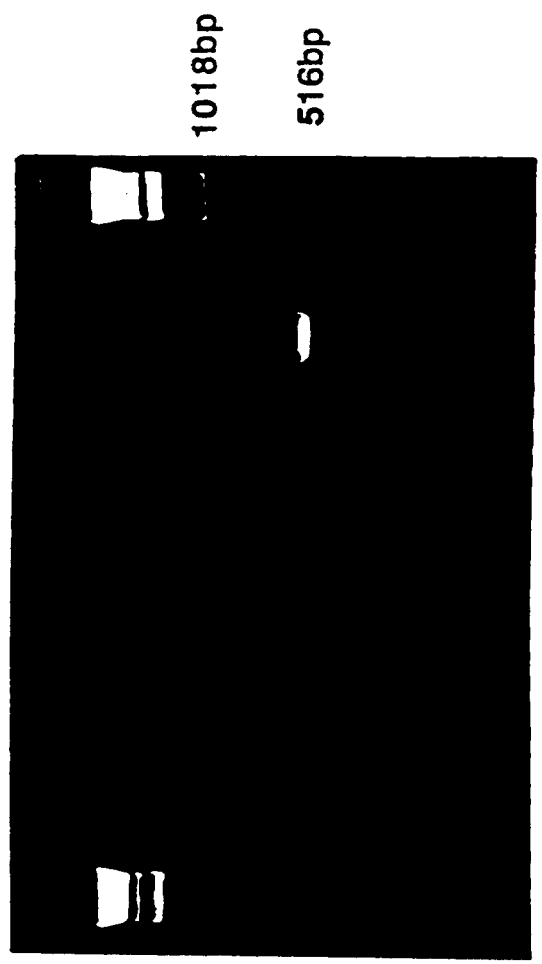
Fig. 5A
Fig. 5B

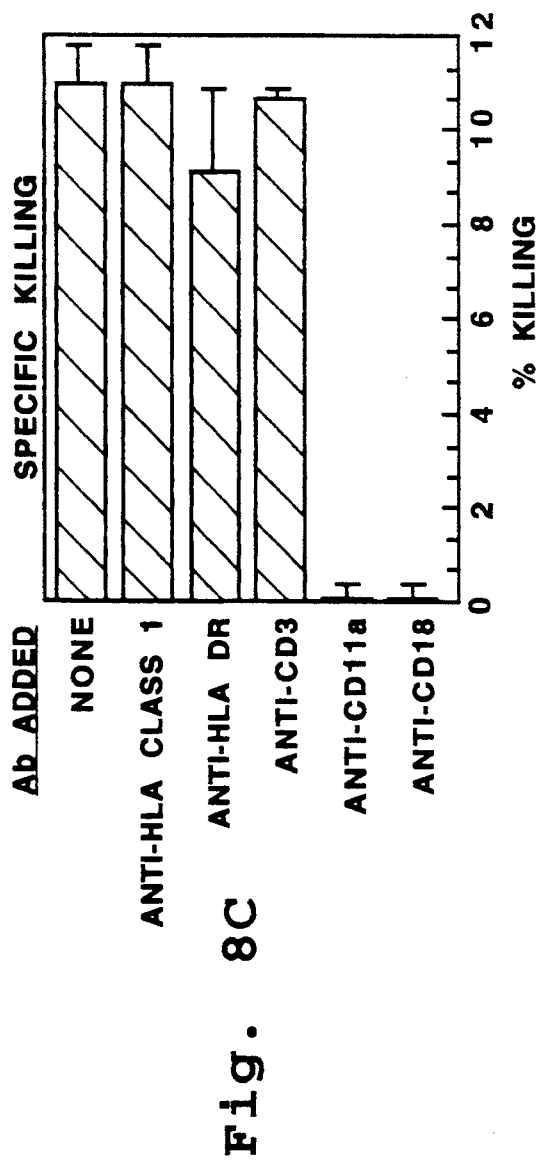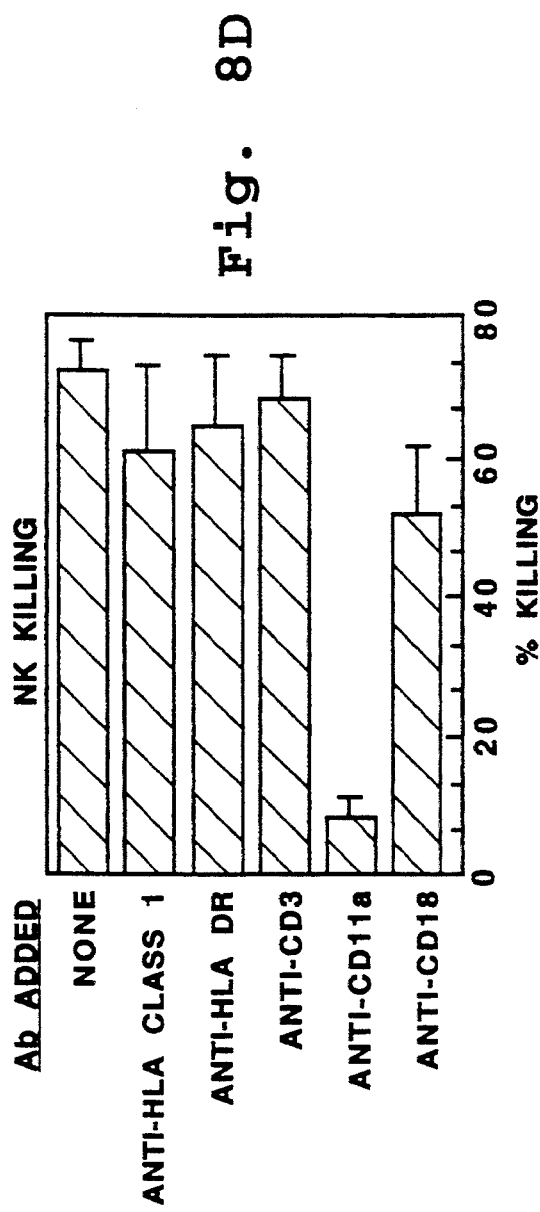

NATURAL KILLER CELL LINES AND CLONES WITH ANTIGEN SPECIFICITY

FIELD OF THE INVENTION

The present invention relates to natural killer cell lines which display cell specific cytotoxity.

REFERENCES

Bender, J., et. al., J. Clin. Invest. 79, 1679–1688 (1987).
Bolhuis, R., et. al., Cell. Immunol..93., 46–57 (1985).
Bordignon, C., et. al., Science 230, 1398–1401 (1985).
Brasile, L., et. al. J. Transplant. Proc. 17, 741–743 (1985).
Brenner, C. A., et. al., Biotechniques (in press) (1989).
Cathala, G., et. al., DNA 2, 329–335 (1983).
Cudkowicz, G., et. al., J. Immunology 7, 291–306 (1964).
Cudkowicz, G., et. al., Transplant. Proc. 15, 2058–2063 (1983).
Dialynas, D. P., et. al., Proc. Natl. Acad. Sci. USA 83, 9–2623 (1986).
Engleman, E. G., et. al., J. Immunol. 127:2124 (1981).
Fathman, C. G., et. al., In Handbook of Experimental Immunology, Vol. 2, 4th Ed. D. M. Weir, L. A. Herzenberg, C. Blackwell, and L. A. Herzenberg, eds. Blackwell Scientific, Edinburgh, pp. 69.1–69.12 (1986).
Fitzgerald-Bocarsly, P., et. al., Immunol. Today 9, 292 (1988).
Fox, D. et al., J. Immunol. 134, 330–335 (1985).
Haskard, D., et. al., J. Immunol. 137, 2901–2906 (1986).
Herberman, R. B., et. al., Science 214:24 (1981).
Hercend, T., et. al., J. Clin. Invest. 75:932 (1985).
Hercend, T., et. al., Immunol. Today 9, 291–293 (1988).
Hynes, R., Cell 48, 549–554 (1987).
Jensen, P., et. al., J. Immunol. 123, 1127–1132 (1979).
Lanier, L. L., et. al., J. Immunol. 136:4480 (1986).
Lefkowitz, M., et. al., J. Hum. Immunol. 19, 139–149 (1987).
LeFor, A., et. al., J., Immunol. 140, 4062–4069 (1988)

Maniatis, T. et. al., Molecular Cloning: A Laboratory Manual, Cold Spring Harbor Press (1982).
Marboe, C., et. al., J. Clin. Immunol. and Immunopath. 27, 141–151 (1983).
Mohagheghpour, N., et. al., J. Immunol. 133, 133–136 (1984).
Nemlander, A., et. al., Cell. Immunol. 89, 409–419 (1984).
Perussia, B. et al. J. Immunol. 133, 180–189 (1984).
Perussia, B., S., et. al., J. Immunol. 130:2133 (1983).
Phillips, W., et. al., J. Immunol. 125, 2322–2327 (1980).
Reynolds, C. W., et. al., Immunol. Today. 8:172 (1987).
Rivas, A., et. al., J. Immunol. 142: 1840 (1989).
Roder, J., et. al., J. Exp. Med. 150, 471–481 (1978).
Rosenberg, S., J. Natl. Cancer Inst. 75, 595–603 (1985).
Sasaki, D. T., et. al., Cytometry 8:413 (1987).
Schmidt, R. et al., J. Immunol. 135, 672–678 (1985).
Shaw, S. et al., Nature 323, 262–264 (1986).
Takada, S., et. al., J. Immunol. 139:3231 (1987).
Trinchieri, G., et. al., Lab. Invest. 50:489 (1984).
Wysocki, L., et. al., Proc. Natl. Acad. Sci. USA 75, 2844–2850 (1978).
Yanagi, Y. et al. Nature 308, 145–149 (1984).

BACKGROUND OF THE INVENTION

Natural killer (NK) cells are defined as lymphocytes which lyse certain transformed or virally infected targets without prior sensitization or restriction for products of the major histocompatibility complex (MHC) (Herberman et al, Bolhuis et al, Trinchieri et al, Reynolds et al). Although T cells (CD3+) have been described with NK-like activity, classical NK cells are large granular lymphocytes which lack CD3 and express CD16 and/or Leu 19 (Lanier et al; Perussia et al, 1983; Hercend et al, 1985, 1988). Despite the fact that NK cells have a limited target cell range, no specific NK associated surface receptor or target ligand has yet been defined, leading to speculation that such effector cells lack a highly refined antigen recognition system. However, work done in support of the instant invention suggests that some NK cells lyse their targets with a high degree of specificity. Lymphocytes of NK phenotype (CD3−, CD16+) were cultured for several weeks with allogeneic microvascular endothelial cells (EC) or lymphoblastoid cell lines (LCLs) in the presence of medium containing growth factors such as IL2. The resulting NK cell lines, which retained their NK phenotype, displayed selective cytolytic activity against their specific stimulator line.

SUMMARY OF THE INVENTION

It is one general object of the present invention to provide a cell preparation containing predominantly natural killer cells, a portion of which adhere to a selected target cell type and acquire the ability to specifically lyse the target cells. The specific—NK cells of this preparation are CD3− and may be CD16+ and/or leu19+. Two selected targets for these selected NK cells are microvascular endothelium and lymphoblastoid cell lines, but cell-targets more generally include tumor cells and infected cells.

Another object of the instant invention is to provide a method of preparing natural killer cells, a portion of which adhere to a selected target cell type and acquire the ability to specifically lyse the target cells. This method includes obtaining a partially purified preparation of natural killer cells, contacting the preparation with the selected target cell type, selecting natural killer cells based on their adhesion to the selected target cell type, and culturing the selected natural killer cells by providing an agent which promotes their proliferation.

The partial purification of this method of preparing natural killer cells may further include removing the monocytes, B-cells, CD3+ and CD5+ cells. Removing these cells may be accomplished by passing the peripheral blood lymphocytes over nylon wool columns followed by incubation of the remaining lymphocytes in the presence of support-bound anti-CD3 and anti-CD5 monoclonal antibodies.

The partially purified natural killer cells may be incubated in the presence of a monolayer of the selected target cell type and the adherent cells selected by washing away the natural killer cells that have not adhered to the target cells. Selected NK cells can be amplified in culture in the presence of cell growth factors, such as IL2.

A further object of the present invention is a method of tumor treatment of a subject. This method of treatment includes obtaining a partially purified preparation of natural killer cells from the subject's blood, contacting the preparation with the tumor cells, selecting natural killer cells based on their adhesion to the tumor cells, culturing the selected natural killer cells by providing an agent which promotes proliferation of the selected natural killer cells, preparing the selected natural killer cells for infusion, and administering the natural killer cells in an infusion. The infusion may further contain a cell growth factor such as interleukin-2. In a specific embodiment of the invention the NK cells are specific to lymphoid cells.

It is yet another object of the invention to provide a preparation of natural killer cells, a portion of which adhere to a selected target cell type and have the ability to specifically lyse the target cells. This preparation is prepared essentially by obtaining a partially purified preparation of natural killer cells, contacting the preparation with a selected target cell type, selecting natural killer cells based on their adhesion to the selected target cell type, and culturing the selected natural killer cells by providing an agent, such as a cell growth factor, which promotes proliferation of the selected natural killer cells.

BRIEF DESCRIPTION OF THE FIGURES

FIGS. 2A-B. Northern blot analysis of an NK (CD3−) cell line (AL45) and the syngeneic T cell (CD3+, CD8+) line (AT45) generated using the allogeneic EC45 line as stimulator in a 3 week culture period.

FIGS. 3a-f. Cytotoxic activity of 3 natural killer cell lines (AL45: a,d; AL158: b,e; AL178: c,f) generated by continuous stimulation with EC lines 45 (a,d), 158 (b,e) and 178 (c,f). AL158 and AL178 were derived from the same individual.

FIG. 5A-B. Message amplification phenotyping of an NK cell line. Messenger RNA from LCL ND, T cell leukemia cells Jurkat and PEER, and the NK-D line were reverse transcribed, amplified using the PCR technique, and the amplified PCR fragments were analyzed on 2% agarose gels.

FIG. 8A-D. Effects of various monoclonal antibodies (mAbs) on the cytolytic activity of a CD3− cell line and a CD3− clone.

DETAILED DESCRIPTION OF THE INVENTION

I. Isolation and Characterization of Stimulator-Cell-Line-Specific Natural Killer Cells Natural killer (NK) cells were isolated from peripheral blood lymphocytes (PBL). Monocytes and B-cells were removed by passage of the PBLs over nylon wool columns and the natural killer cells were then obtained by one of the following methods:

(1) positive selection by sorting with a fluorescence activated cell sorter or panning (Engleman et al) using anti-Leu 11c monoclonal antibody (mAb) (Example 1: less than 0.1% CD3+), or (2) by removing unwanted cells using a fluorescence activated cell sorter or panning using anti-CD3 and anti-CD5 monoclonal antibodies (Example 4: less than 0.5% CD3+).

CD3−, CD16+ cells were incubated on monolayers of the specific stimulator cell lines. Adherent cells were cultured with irradiated stimulator Cells in the presence of IL2-containing medium, and following 6 weeks of continuous expansion the resulting cell lines were analyzed. Table 1 lists specific stimulator cell lines and the names assigned the corresponding natural killer (NK) cell line.

TABLE 1

| NK cell line | Stimulating cell line |
|---|---|
| A. Microvascular Endothelium | |
| AL33 | EC33 |
| AL37 | EC37 |
| AL44 | EC44 |
| AL45 | EC45 |
| AL158 | EC158 |
| AL178 | EC178 |
| B. Lymphoblastoid Cell Lines | |
| Line A | Arent |
| Line B | Arent |
| clone A | |
| Line D | Arent |
| clone 3 | |
| Line 110 | ND |
| Line 121 | MSAB |

Figure 1:
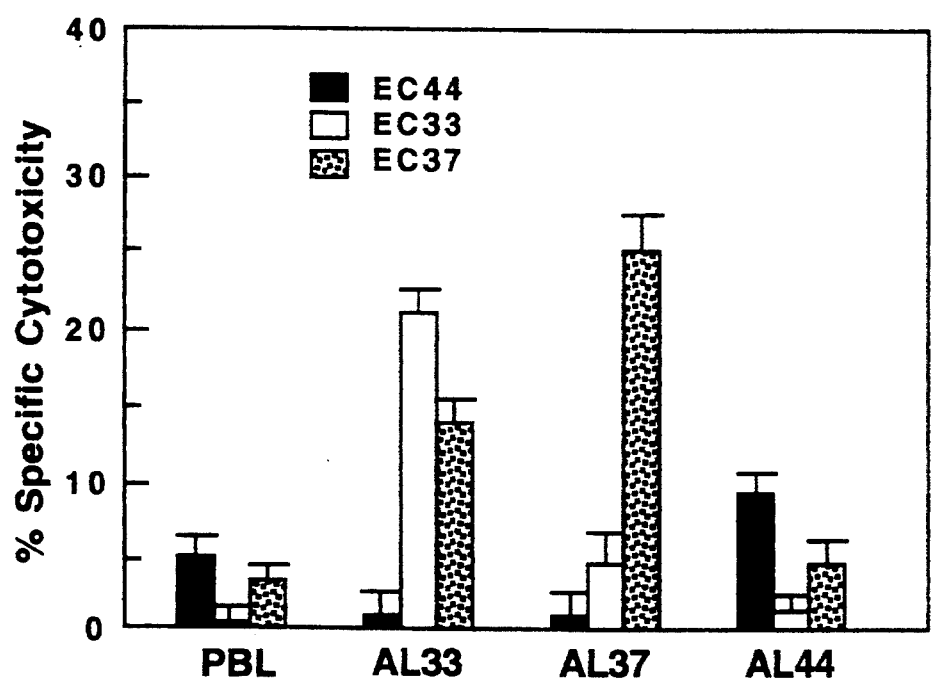
FIG. 1. Cytotoxic activity against 3 different EC lines (EC44, EC33, EC37) by monocyte-depleted PBL and EC-adherent lymphocytes recovered after a 90 min binding of PBL to EC33 (AL33), EC37 (AL37), and EC44 (AL44).

(i) Microvascular Endothelial Stimulator Cells In initial studies performed in support of the present invention, monocyte-depleted PBL from healthy donors were cultured overnight in IL2 containing medium and then added to three different allogeneic microvascular endothelial cell (EC) lines. These cells, prepared from human foreskin obtained from infants undergoing circumcision, represent normal, untransformed EC and grow as monolayers adherent to plastic. After a 90 minute coincubation, the EC adherent lymphocytes were recovered and further analyzed. These cells were highly enriched for cells of NK phenotype (CD3−, CD16+) (data not shown). When used as effectors in 4 hour cytotoxicity assays (Example 1), these NK-enriched cells were cytotoxic for ECs (FIG. 1). Furthermore, lymphocytes adherent to each of 3 allogeneic EC lines demonstrated preferential cytotoxicity against the line to which they were originally bound (FIG. 1). Although this result was highly reproducible, it was nonetheless a surprising finding since, except for the 90 minute co-incubation with stimulator EC, the effector cells had not been previously exposed to their targets.

Next, EC-adherent CD16+, CD3− lymphocytes were highly purified by a combination of panning and sorting (Examples 1 and 2). These selected NK cells were then co-cultured for 3 weeks with one of three allogeneic microvascular EC lines (Example 2) in the presence of IL2-containing conditioned medium. These NK populations underwent up to 5-fold expansions during the 3 week culture period and not only adhered rapidly when initially added to original stimulating-EC monolayers, but continued to grow in an EC-adherent fashion. The expansion of these NK cells was dependent on the continued presence of EC monolayers, as the same cells cultured in parallel in identical medium but without EC grew minimally. Surface immunofluorescent staining of the propagated NK lines, using a panel of mAbs including OKT3, Leu 4, and WT31, demonstrated that they were negative both for CD3 and for the T cell receptor (TCR). Also, these NK cell lines were 92–96% CD2+, 48–56% CD8 dull positive, and 70–90% CD16+.

Syngeneic T cells, treated identically to the above NK lines, also proliferated in the presence of allogeneic EC monolayers and conditioned medium. However, these cells did not grow as EC adherent lines and were greater than 99% CD3+, WT31+ and 90% CD8+ (not shown).

To further document the absence of T cell receptor expression in the CD3−, CD16+ cell lines, Northern blot analyses (Example 2) were performed by probing total cellular RNA from these cells and their syngeneic T cells with complementary DNA fragments derived from either the beta or gamma chain of the T cell receptor (Yanagi et al; Dialynas et al). As shown in FIG. 2a and b, no TCR beta or TCR gamma messages were detected in the CD3−, CD16+ cell line. In contrast, TCR beta transcripts of 1.3 and 1.0 Kb were identified in the syngeneic T cell line as well as in two malignant T-cell lines, HPB-ALL and PEER (FIG. 2a, lanes 4–6). When hybridized to the TCR gamma probe, PEER and HPB-ALL RNA revealed a 1.6 Kb band as previously reported (FIG. 2b, lanes 5 and 6) (Bolhuis et al). Total cellular as well as poly-A(+) RNA from an Epstein-Barr virus transformed B cell line were appropriately negative for both blot hybridizations. Full-length gamma-actin transcripts were detected in all RNA samples, including the sampled derived from the CD16+ NK line, confirming the presence of hybridizable RNA in our preparations (not shown). These results indicate that the CD16+ cytolytic NK cell lines lack detectable T cell receptor RNA, a result which is not surprising in view of the absence from the surface of these cells of detectable CD3 and TCR chains.

The CD3/TCR negative, CD16+ cell lines were evaluated for their ability to lyse the relevant, stimulating EC line or irrelevant lines in 4 hour chromium-release assays (Example 3). As shown in FIG. 3a, AL45 was highly cytotoxic—50% cytotoxicity at a 1:1 Effector/Target (E/T) ratio—toward EC45 and was unable to kill the two irrelevant lines, EC35 and 129. AL158 (FIG. 3b) and AL178 (FIG. 3c) were derived from the same individual and were stimulated in parallel by EC158 and EC178, respectively. Reciprocal killing experiments were performed to address the possibility that target sensitivity was the major determinant of EC susceptibility to lysis by any of the NK lines. As shown, AL158 and AL178 displayed strongly preferential cytotoxicity toward the relevant stimulating EC line, although AL178 also exhibited detectable lysis of EC158 and EC180 (15.9 and 16.4% cytotoxicity, respectively, at a 1:1 E/T ratio). At E/T ratios higher than 1:1, the extent of nonspecific killing rose, but even at E:T ratios of 25:1, lysis of the stimulating EC was greater than that of irrelevant EC (data not shown). All 3 NK lines were highly cytotoxic (greater than 70% cytotoxicity at a 1:1 ratio) to the NK sensitive K562 line (not shown).

Figure 3F:
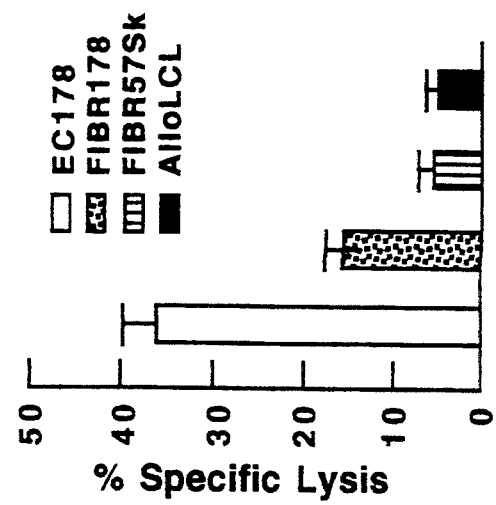
Figure 3E:
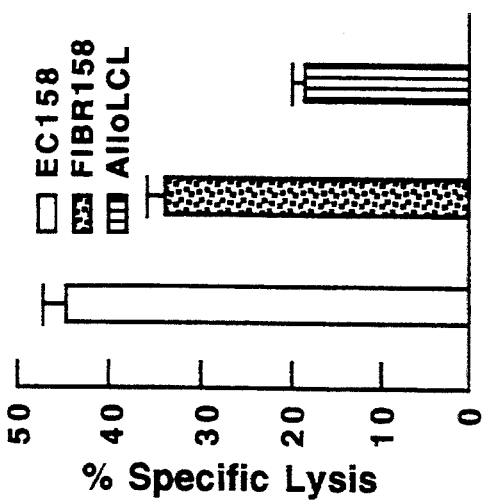
Figure 3D:
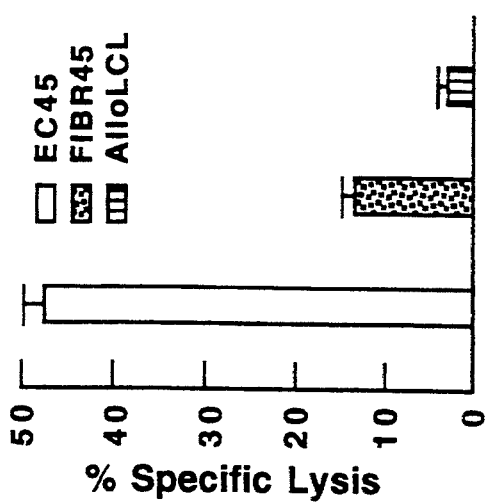

To investigate whether this phenomenon was specific to EC targets, several other cell types were utilized as targets in cytotoxicity assays. At an E/T ratio of 1:1, AL45 (FIG. 3d), AL158 (FIG. 3e), and AL178 (FIG. 3f) lysed their stimulating EC lines more efficiently than the respective syngeneic fibroblast lines; also AL178 demonstrated a greater degree of cytotoxicity toward the "relevant" fibroblast line than an irrelevant fibroblast line (FIG. 3f). This raises the possibility that EC and fibroblasts share a putative allogeneic target molecule(s) but that EC are more sensitive to lysis, or that these molecules are simply more highly expressed on EC. Epstein-Barr virus transformed lymphoblastoid cell lines from unrelated individuals (AlloLCL) were not efficiently lysed by any of the 3 NK lines (FIG. 3d, e, f), making it unlikely that the observed lysis of EC simply reflected the lymphokine-activated killer (LAK) function common to IL2-activated cells (Lefor et al).

To examine the role of various cell surface molecules in the lysis of EC, blocking experiments were performed using a panel of monoclonal antibodies. For these experiments, antibodies were added at concentrations of 10–25 μg/ml directly to the cytotoxicity assays. As expected, neither anti-Leu 4, which recognizes the CD3 molecule, nor WT31, which recognizes a monomorphic determinant on the T cell receptor complex, had any effect on these CD3/TCR negative cells (data not shown). Similarly, W6/32 (specific to Class I HLA determinants) antibody failed to inhibit cytotoxicity, suggesting that class I HLA molecules do not serve as the relevant targets on EC. In contrast, anti-LFA-1 (specific to LFA-1 α and β chains) consistently inhibited cytotoxicity (>50%), which presumably reflects the role of the LFA-1 molecule in lymphocyte binding to EC (Bender et al; Haskard et al). However, it seems unlikely that LFA-1 is responsible for the specificity of cytotoxicity since in other systems LFA-1 mediated adhesion is not antigen-specific (Yanagi et al).

The CD2 molecule has been reported to play an important role in the triggering of early CD3− stage I and II thymocytes (Fox et al) as well as NK clones (Schmidt et al) and on this basis this molecule has been postulated to be the receptor for NK target antigens on NK-susceptible populations. This is an interesting possibility in regard to the findings reported here, since CD2 can mediate cellular adherence as well as activation, and the antigen-specific cytotoxicity mediated by our NK lines appears to occur, in part, as a consequence of specific adherence. However, the CD2LFA-3 adhesion pathway is thought to be antigen-independent (Shaw et al) and peptide variability within the CD2 molecule has not been demonstrated. Furthermore, anti-Leu 5b mAb (specific to the CD2 cell surface molecule) did not substantially inhibit specific lysis in this study (not shown), although the possibility exists that epitopes on the CD2 antigen not recognized by this antibody may be involved. The CD16 molecule (Fc gamma receptor) was present on the EC-specific NK cytolytic lines and since this receptor is capable of mediating antibody dependent target lysis, a role for CD16 in the specific cytolysis observed was considered. However, saturating concentrations of anti-Leu 11c (specific to the Fc gamma receptor) mAb failed to inhibit cytotoxicity (not shown), making it unlikely that CD16 plays a critical role in the EC directed killing. More importantly, the reciprocal cytotoxicity experiments (FIG. 3 b, c), in which antigen-specific lysis was shown to occur in the presence of identical serum and distinct targets, virtually rules out this possibility. Because EC-adherent lymphocytes, enriched in CD16+ cells, appear to specifically lyse the EC to which they initially bound (FIG. 1) and since the CD16+ EC-reactive NK lines mediate cytotoxicity in an allospecific fashion (FIG. 3), it was also investigated whether these lines adhered specifically to the relevant stimulating EC. AL158 and AL178 were removed from their respective EC stimulators and tested for adherence in 20 minute binding assays (Table 2). A shortened incubation was necessitated by the potent cytotoxic potential of the effector cells. AL158 and AL178 were generated from the same individual and stimulated with the indicated EC lines as described in the Example 2. Upon recovery after 3 weeks, the lymphoid cells were $^{51}$Cr-labeled and utilized as effectors in an adherence assay as previously described (Bender et al) with a 2:1 lymphocyte/EC ratio and a 20 minute incubation. The values in Table 2 represent the percentage of labeled cells which remain adherent after the incubation and washes.

TABLE 2

|       | AL158        | AL178        |
|-------|--------------|--------------|
| EC158 | 50.6 ± 5.1   | 34.7 ± 3.9   |
| EC178 | 39.5 ± 3.2   | 44.2 ± 2.6   |
| EC180 | 37.5 ± 3.6   | 33.6 ± 2.1   |

EC180 served as a mutually irrelevant target, to which AL158 and AL178 bound quite well (37.5 and 33.6%, respectively). This is not surprising due to the advanced state of lymphocyte activation, and the known induction of adhesion molecules, such as the VLA antigens (Hynes) during activation. AL158 and AL178 adhered to the two irrelevant EC to the same degree, but demonstrated enhanced binding to the relevant stimulating EC lines 50.6% and 44.2%, respectively; the probability of random occurrence of these data are $p<0.05$ for AL158 and $p<0.01$ for AL178. Identical reciprocal binding experiments with EC-activated T cell lines failed to demonstrate any specific binding, despite allospecific cytotoxicity (data not shown). These results indicate that the cytotoxic NK lines bind with relative specificity for their stimulating EC, and suggest that the basis for their specific cytotoxicity may lie, at least in part, with specific binding.

Figure 4:
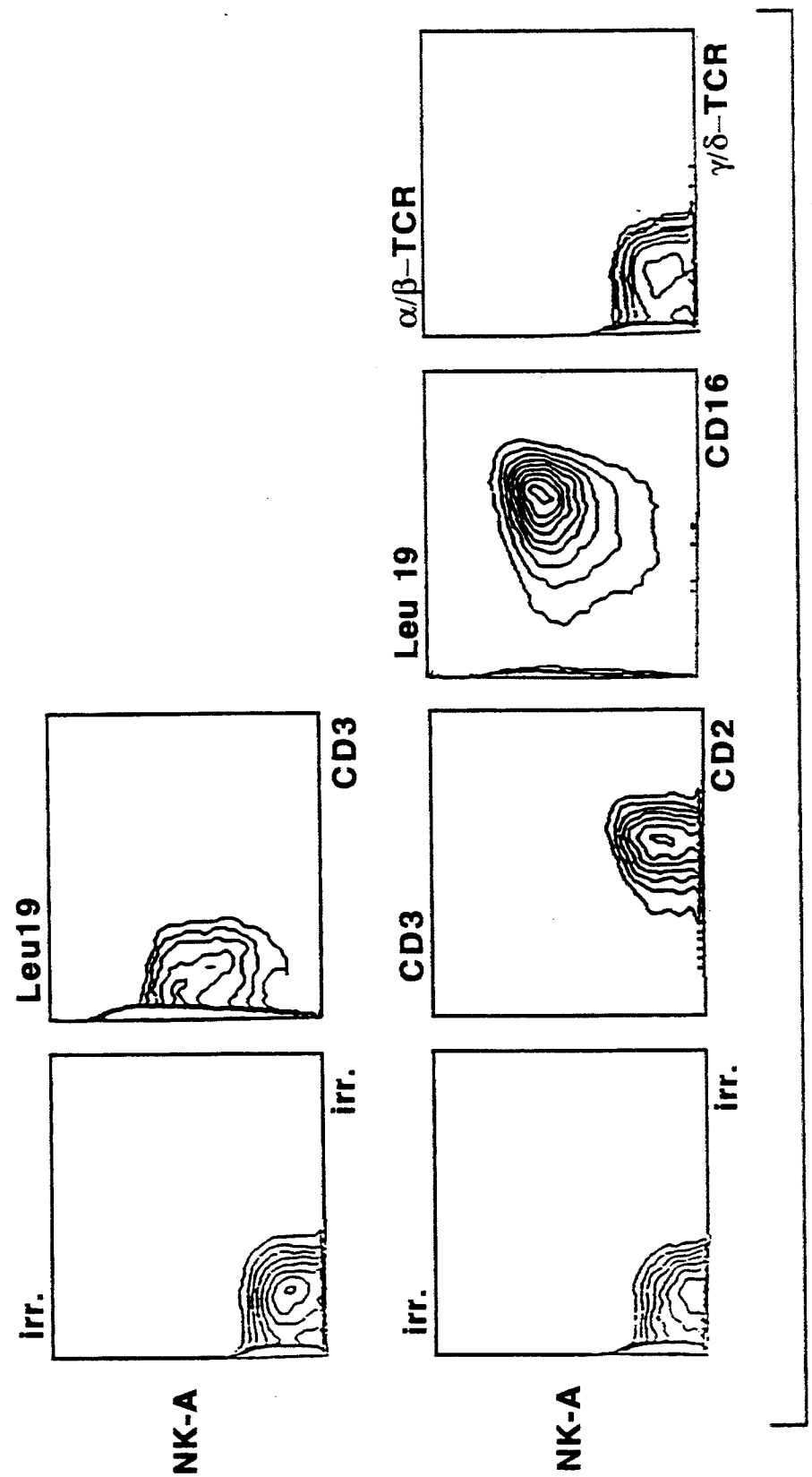
FIG. 4. Two-color flow cytometric analysis of cell surface antigens on a cell line derived from fresh CD3−, CD16+ lymphocytes.
Figure 6A:
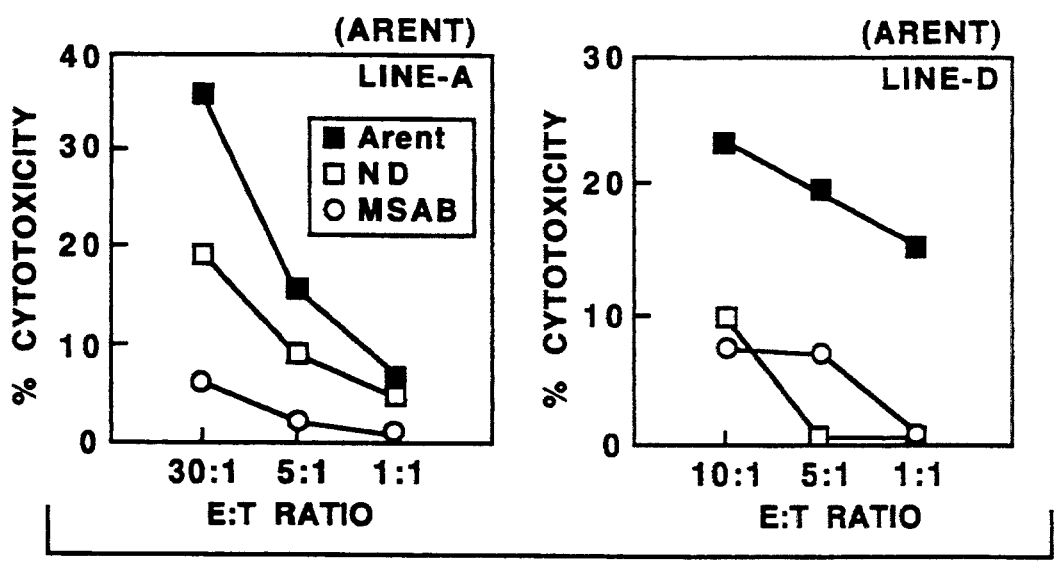
FIG. 6. Cytotoxic activity of CD3− cell lines and clones.
Figure 6B:
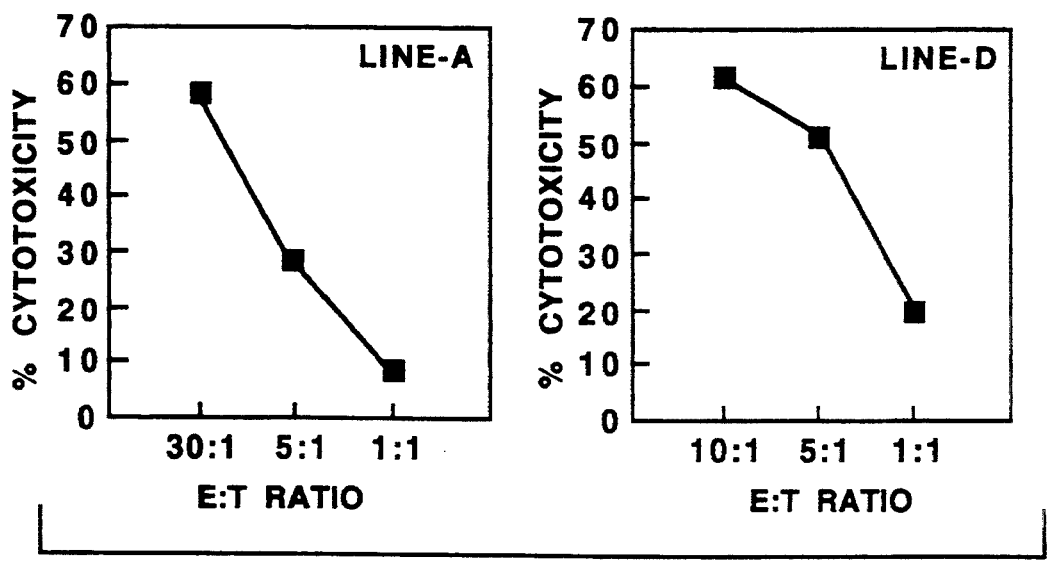
Figure 6C:
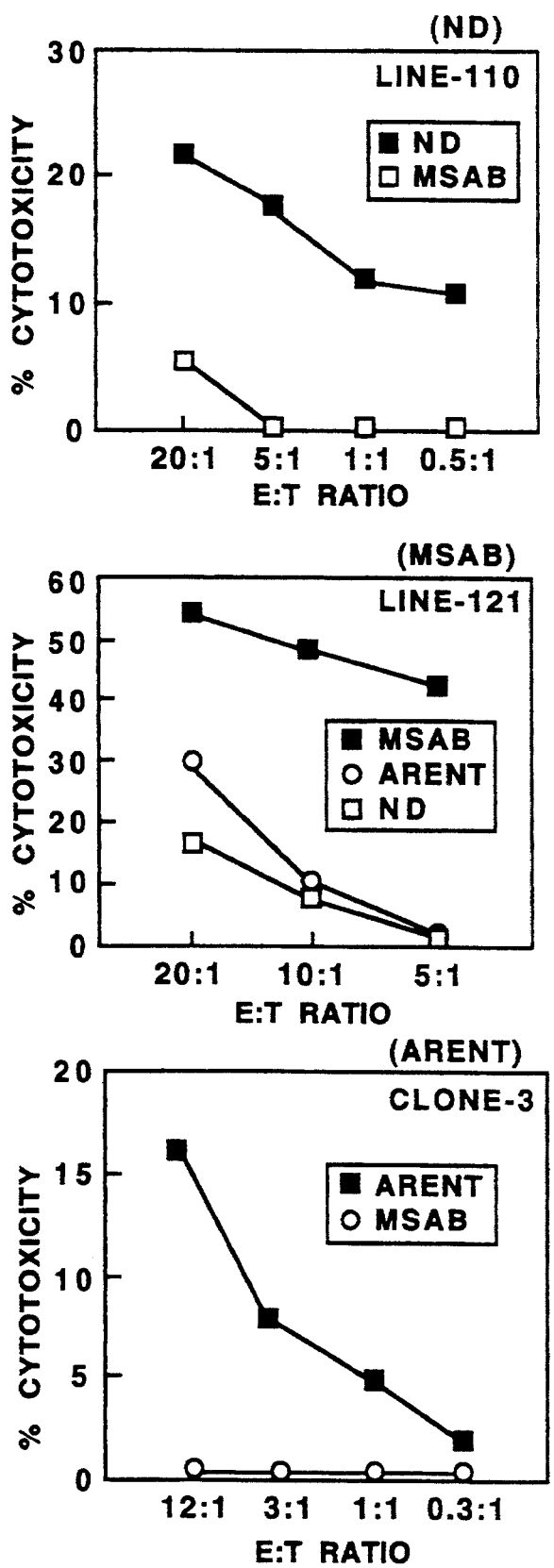
Figure 6D:
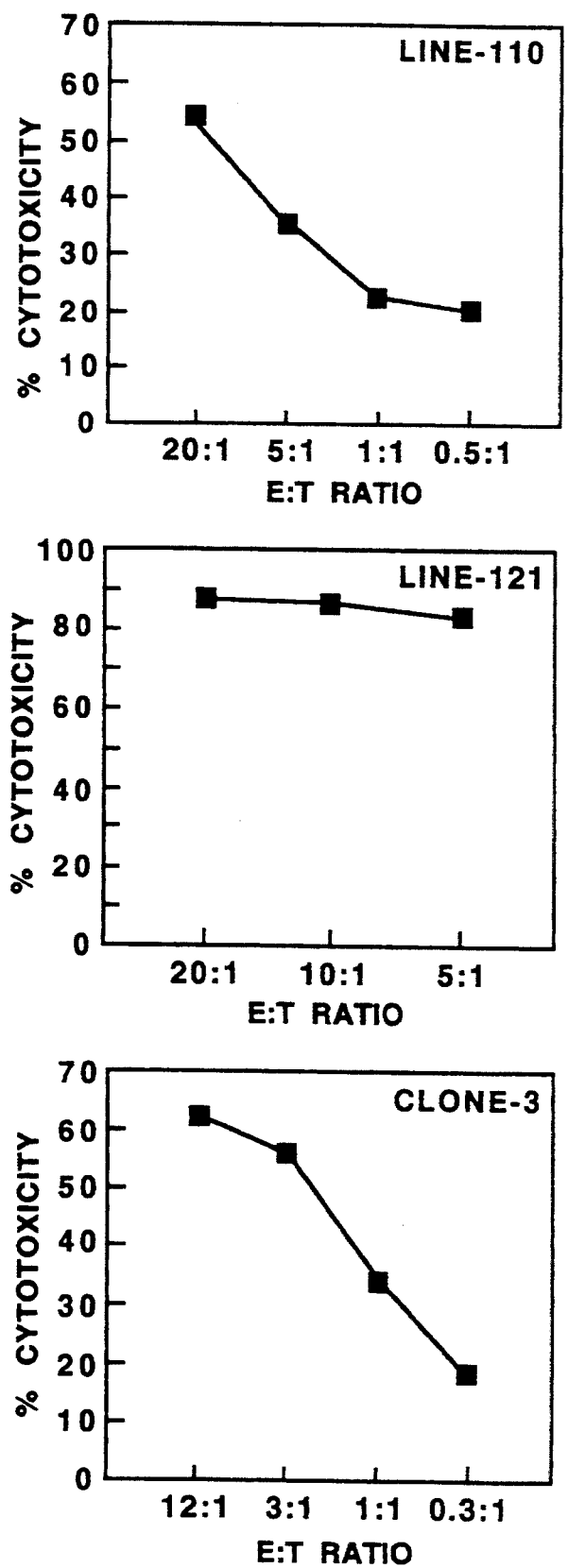

(ii) Lymphoblastoid Stimulator Cell Lines Adherent cells were cultured with irradiated lymphoblastoid cell lines (LCL), these cell lines are Epstein-Barr virus transformed B-cells, in the presence of medium containing growth factors such as IL2 (Example 4). Following six weeks of continuous expansion the resulting NK cell lines were analyzed in a flow cytometer for the expression of several surface markers. As shown in FIG. 4, for a representative line, all cells express CD2, CD16 and Leu 19, but lack expression of CD3, the α/β TCR (antibody WT31) or γ/δ TCR (antibody TCR-γ/δ- 1).

Multiple clones were derived by limit dilution culture of these lines (ie., the cells were seeded in microtiter wells at approximately. 0.5 cells per well), even though the cloning efficiency was low (0.5-1.0%) and the growth rate slow (doubling time 48 hours). Two clones were generated in sufficient numbers to study in parallel with parental cell lines. NK cell lines and clones were separated from feeder cells over Ficoll-Hypaque ™ gradients and stained by direct immunofluorescence. Samples of $10^4$ cells each were analyzed in an Ortho System 50H cell sorter. Table 3 summarizes the results of immunofluorescence analysis of the natural killer lines and clones (n.d. indicates the value was not determined).

TABLE 3

Flow Cytometric Analysis of Cell Surface Antigens on NK Lines and Clones

|          | CD3 | CD2  | CD16 | Leu 19 |
|----------|-----|------|------|--------|
| Line A   | —   | +    | +    | +      |
| Line 110 | —   | +    | +    | +      |
| Line 121 | —   | +    | —    | +      |
| Line D   | —   | +    | —    | +      |
| clone 3  | —   | n.d. | +    | +      |
| clone A  | —   | n.d. | —    | +      |

As shown, all NK cell lines were CD3— and leu19+, but only 3 of 6 were CD16+. To analyze TCR and CD3 messages in these cells, we reverse transcribed total cellular RNA to obtain cDNA, which was subsequently amplified by the polymerase chain reaction technique, using TCR and CD3 specific primers (Example 5). Probing of the amplified messages revealed a TCRγ sequence but no other TCR messages and no CD3 messages (FIGS. 5A-B). Studies of 3 of 3 similarly derived NK lines revealed γ TCR message but no other TCR and no CD3 messages (not shown).

To determine whether these cells had cytolytic activity, representative lines and clones were tested as effectors in 4 h $^{51}$Cr-release assays (Example 7-B) against the original stimulator LCL as well as irrelevant LCLs and NK sensitive K562 cells. As shown in FIG. 6, all NK lines and clones exhibited potent, dose-dependent lysis of K562 cells. This is not surprising in light of the surface phenotype (CD3—, CD16+, Leu 19+ or CD3—, CD16—, Leu 19+) of the effectors.

Further, the NK lines and clones also lysed LCL targets (FIG. 6). Although the potency of this killing was weaker than the lysis of K562 targets, lysis of the original stimulator LCL exceeded that of the other LCLs. Similar results were obtained from NK lines or clones generated from multiple donors to 3 different stimulator LCL (FIG. 6), suggesting that the apparent specificity of lysis is not merely a consequence of differential sensitivity of the target LCL to NK or LAK (lymphokine activated killer) cell mediated lysis. Both CD3—, CD16+ and CD3—, CD16— lines demonstrated selective cytolysis of their stimulator LCL, making it unlikely that the CD16 molecule (Fc γ receptor) played a role in the lysis of these targets (data not shown).

Figure 7A:
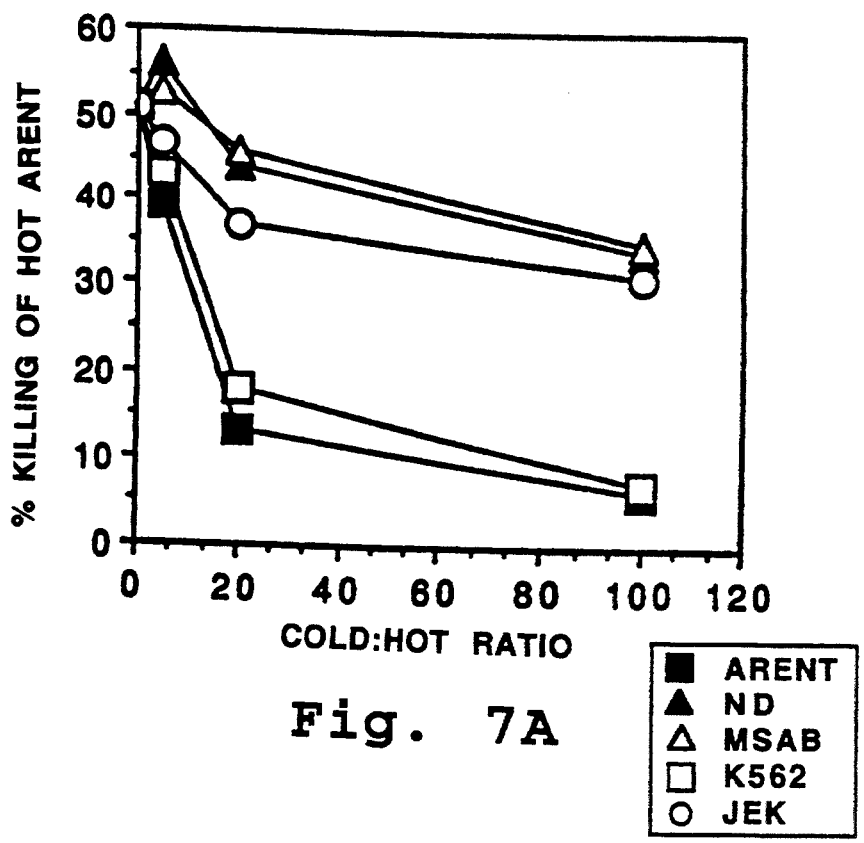
FIG. 7A-D. Effect of unlabeled (cold) target cells on the cytolytic activity of a CD3− line and a CD3− clone.
Figure 7B:
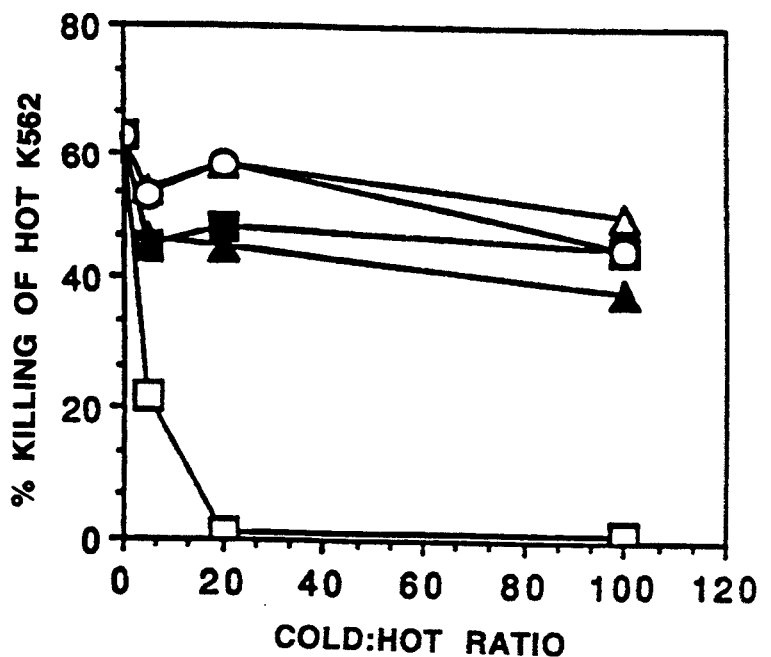
Figure 7C:
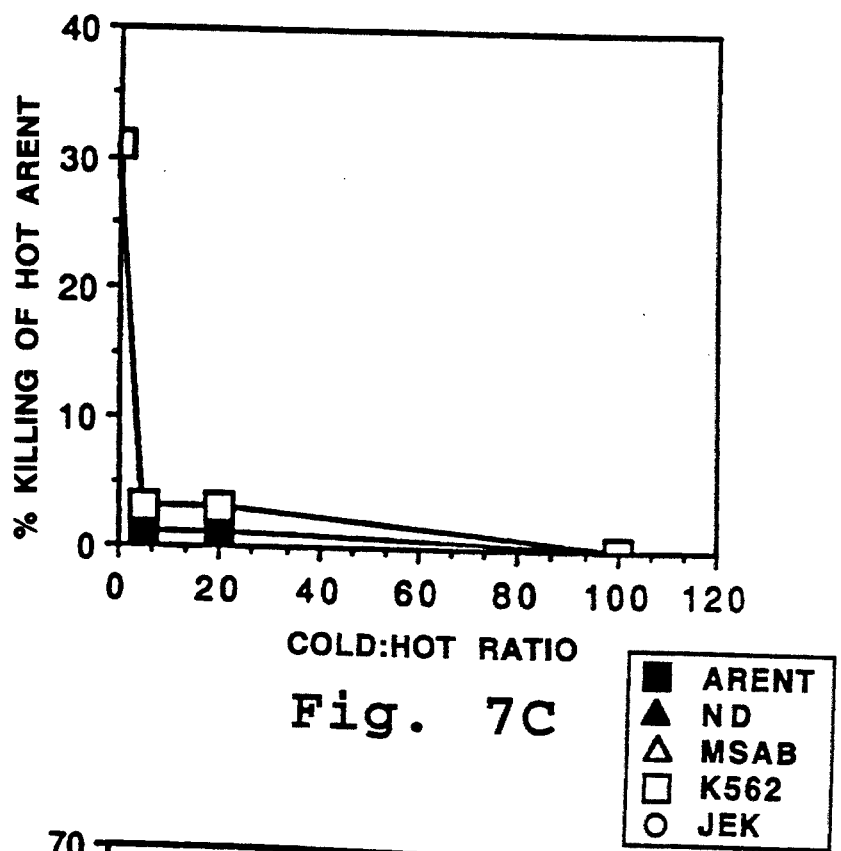
Figure 7D:
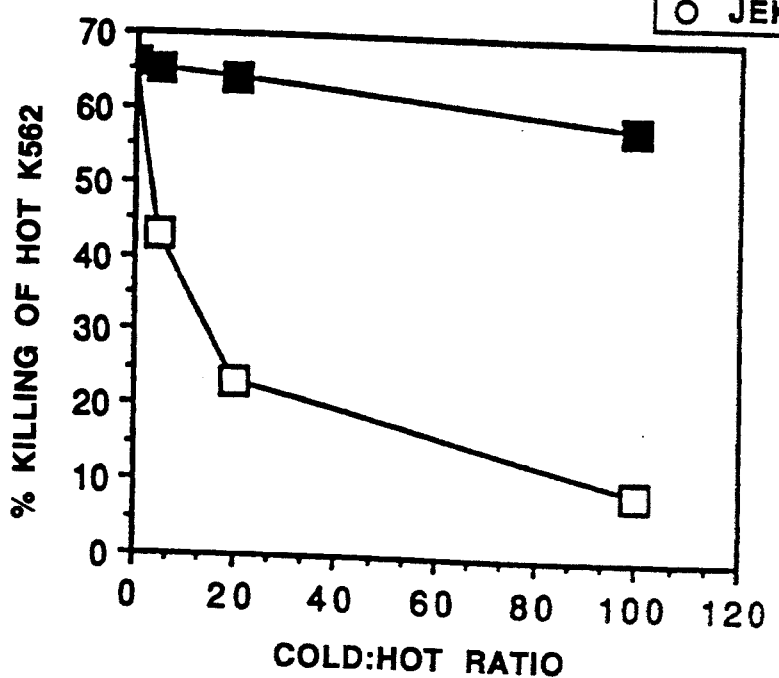
Figure 8A:
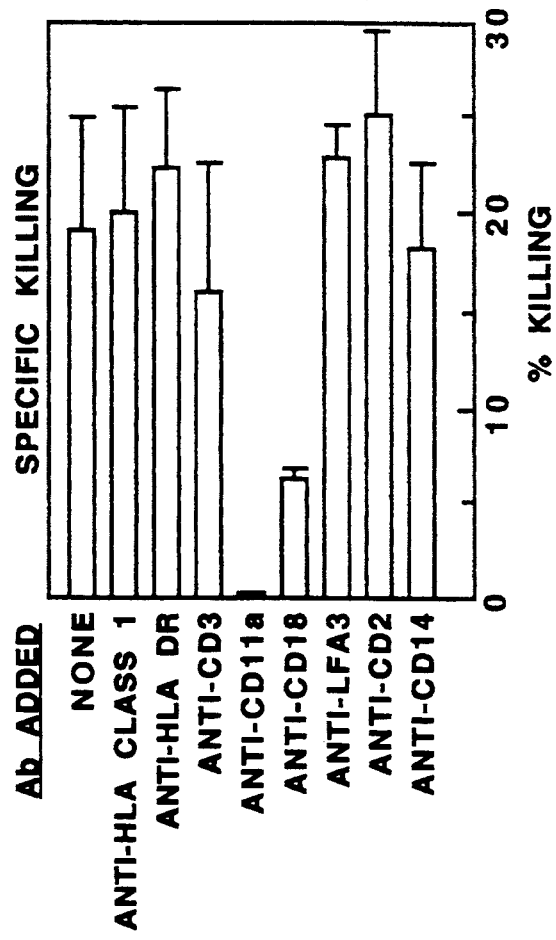
Figure 8B:
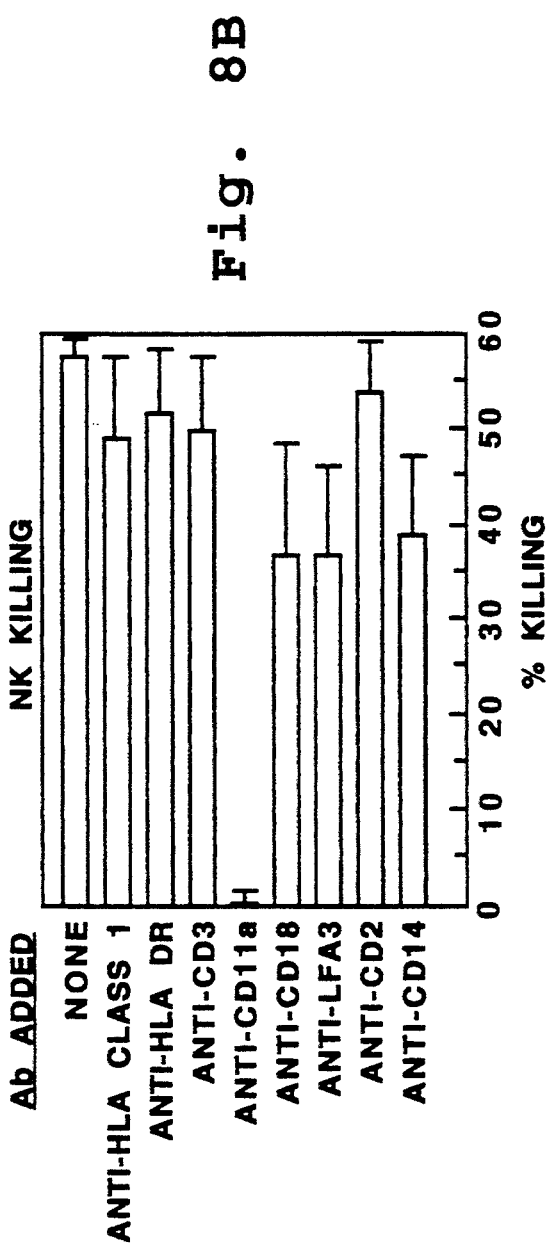

To further explore the specificity of cytolysis, the LCL stimulated NK lines and clones were used as effectors in cold target inhibition assays (Example 7-C). In these experiments cold (unlabeled) target cells (K562, specific stimulator LCL, or irrelevant LCLs) were tested in varying numbers for the ability to inhibit cytolysis of $^{51}$Cr-labeled NK sensitive K562 cells or specific stimulator LCL. As shown in FIG. 7B and 7D, specific killing of the original stimulator line, ARENT, was inhibited by the addition of unlabeled ARENT or K562 cells but not by the addition of irrelevant unlabeled LCL. As shown in FIG. 7A and 7C, unlabeled K562 cells inhibited the lysis of $^{51}$Cr-labeled K562 cells, whereas unlabeled ARENT cells had little if any inhibitory effect on the lysis of K562.

The role of cell surface molecules involved in the NK killing (K562 target) and specific LCL killing by these NK lines and clones was examined using cytotoxicity assays carried out in the presence of selected mAbs (Example 8). As shown in FIGS. 8A-D only anti-CD11a (LFA-1α), which is known to inhibit a variety of interactions between leukocyte effectors and their targets, completely inhibited killing of both targets. An anti-CD18 (LFA-1β) antibody (specific for the β chain of LFA-1) partially inhibited lysis of both targets, however inhibition was more potent when the specific stimulating LCL was tested. In contrast, antibodies to CD3, HLA class I, or HLA-DR at concentrations as high as 25 ug/ml had no detectable effect on the lysis of either target.

(iii) Summary

All of the CD3−, Leu 19+ and/or CD16+ lines and clones described herein lysed their specific allogeneic stimulator cell line. Although absolute specificity for original stimulator cell line was not observed the NK lines lysed their specific stimulator cell lines to a greater extent than irrelevant cell lines. The selective killing was not due simply to differences in sensitivity to cytolysis between various cell lines, since cell lines susceptible to lysis by some effector lines were not susceptible to lysis by others. Furthermore, the results cannot be explained by the presence of contaminating T cells in the cultures, since no CD3, α/β TCR, or γ/δ TCR antigens could be detected by immunofluorescence analysis, and neither anti-CD3 nor anti-HLA mAbs, which are potent inhibitors of T cell mediated lympholysis (Rivas et al), inhibited the killing by the NK lines and clones. In addition, the failure to detect messenger RNA for CD3, or TCRα, β, or δ with an extremely sensitive technique rules out the possibility that the effector lines express a conventional T cell antigen receptor structure. Nonetheless, all of the lymphoblastoid cell lines studied to date contain a message for TCRγ; whether these γ chains are expressed on the surface of these LCLs and play a functional role remain to be determined.

It is important to emphasize that the NK lines and clones of the present invention were derived from CD3− lymphocytes which adhered to the particular cell line chosen for use as a stimulator. We have also generated NK lines and clones from single CD3− cells cultured without an initial adherence step in the presence of allogeneic LCL and high (>50 U/ml) concentrations of recombinant IL2. However, while this approach yielded a large number of rapidly growing NK clones, the vast majority of these clones failed to demonstrate specific lysis of their feeder LCL (data not shown). This suggests that an initial adherence step as well as an avoidance of high concentrations of IL2 in the culture medium may be important factors in the selective growth of the LCL-specific NK lines and clones.

Taken together, these findings indicate the existence of CD3/TCR negative antigen-specific killer cells which are highly cytotoxic for specific stimulator cell lines. Since these killer lines (i) lack CD3− associated T cell receptors, (ii) are CD16 and/or leu 19 positive, and (iii) lyse NK sensitive targets, they are most appropriately designated natural killer cells (Fitzgerald-Bocarsly et al).

II. Utility

Natural killer (NK) cells have traditionally been characterized as cells found in unimmunized normal animals that have the ability to bind and destroy (1) tumor cells, and (2) cells modified chemically, by viruses, some bacteria, or fungi (Tizard). More recently NK cells have been further defined as CD3−, T-cell receptor (α, β, γ, δ) minus (TCR-) large granular lymphocytes. Commonly expressed cell surface markers are CD16 and/or NKH-1 (Leu 19) in humans and NK-1.1/NK2.1 in mice (Fitzgerald-Bocarsly et al). The cytolytic reactions mediated by NK cells do not require expression of class I or II Major Histocompatibility Complex (MHC) molecules on the target cells (Fitzgerald-Bocarsly et al).

Although NK cells have not previously been believed to mediate cytotoxicity in an antigen-specific manner the results of experimental animal bone marrow grafts demonstrate that NK cells are the effectors of hybrid resistance to parental grafts (Bordignon et al). The phenomenon of hybrid resistance appears to be genetically restricted and directed at the products of the non-codominant hematopoietic histocompatibility (Hh) genes (Cudkowicz et al, 1964) which are linked to the MHC complex in the mouse (Cudkowicz et al, 1983). The present invention demonstrates that some NK cells are, in fact, capable of specific target cell adherence and lysis when the NK cells have been preselected against a particular target cell line and subsequently amplified in medium containing growth factors such as IL2.

A. Applications to Immunotherapy

Since target cells for natural killer cells include tumor cells, such as lymphomas and some carcinomas, tumor cell-specific NK cells have applications in adoptive immunotherapy (AIT). AIT is the transfer of active immunological reagents with anti-tumor reactivity, such as tumor cell-specific NK cells, to a tumor containing host (Rosenberg). The target-specific NK cells of the present invention have several advantages for use in AIT:

1) tumor-specific NK cells can be selected by adhesion to the specific tumor cells;
2) tumor-specific NK cells have the ability to be expanded in culture (eg., Table 3, clone 3 and clone A); and,
3) tumor-specific NK cells can be generated from the peripheral blood lymphocytes of the tumor-bearing individual and thus immunotherapy with these NK cells introduces only autogenous cells.

Adoptive immunotherapy with tumor-specific NK cells should be coupled with the administration of IL2 or other appropriate growth factor(s) to insure anti-tumor activity and proliferation of the NK cells.

For AIT large numbers of lymphocytes can be generated from a tumor-bearing patient by repeated leukaphereses (Rosenberg). Typically, initial studies are performed on patients who have failed conventional treatment approaches. Tumor-specific NK cells are generated by isolation of CD3−, CD3−/CD16+, or CD3−/leu19+ lymphocytes followed by adhesion to the specific tumor cell and removal of non-adhering cells (e.g., as described above for lymphoblastoid cells). The NK cells are then proliferated in culture in the presence of growth factor containing medium and the stimulator cell line. Large numbers of the NK cells (eg. greater than $10^{10}$) are isolated and infused into the tumor-bearing patient with simultaneous administration of IL2. Side effects of the treatment and status of the tumor are monitored.

One of the natural functions of NK cells is to provide protection against infection; accordingly, adoptive immunotherapy of infectious diseases is another clinical application of target-specific NK cells. The LCL target cells of the instant invention are EBV infected and have been successfully targeted with LCL-specific NK cells. Other virally transformed cells can also serve as specific-NK stimulator cell lines. For example, HIV-I infected T-cells can be used as a stimulator cell line; a preparation of such HIV-I-infected-cell specific NK cells can be tested as a useful therapeutic agent for the treatment of human acquired immune deficiency.

B. Graft Rejection

Previous attempts to absorb NK activity with target cells have suggested heterogeneity of both NK recognition and target structures (Roder et al; Jensen et al; Phillips et al). The EC target molecules of the NK lines of the present invention do not appear to be MHC antigens. Other candidates include (1) the endothelial-monocyte antigens, proposed to be responsible for acute renal allograft rejection in HLA-identical grafts (Brasile et al), and (2) the postulated MHC-linked antigenic systems equivalent to the Hh antigens in the mouse. Conceivably, the endothelium may express a set of polymorphic antigens, distinct from HLA, which serve both as adhesion molecules and targets of lysis for NK cells. However, since target-specific NK cells against LCL have also been obtained by the methods of the instant invention, it is clear that the antigens recognized by these effectors are expressed on a variety of cell types.

Studies of organ allograft recipients in animals and man have demonstrated early graft invasion by phenotypic and functional NK cells (Nemlander et al; Marboe et al); further, the presence of such cells is predictive of subsequent graft rejection (Marboe et al; Lefkowitz et al). Accordingly, further definition of NK cell-microvascular EC interactions may increase understanding of the graft rejection mechanisms.

In order to identify agents useful in modulating graft rejection, a variety of target-specific NK lines are generated in order to define the range of this novel antigen receptor system. The stimulator cell lines and a bank of monoclonal antibodies are then used to examine the signals involved in NK/target cell recognition, adhesion, and lysis (e.g., as described in Section I above). Monoclonals that will block specific NK/target cell interactions would be useful agents to modulate host graft rejections.

The following examples illustrate, but in no way are intended to limit the present invention.

MATERIALS AND METHODS

Cell lines. Peripheral blood lymphocytes were isolated by standard procedures. Microvascular endothelial cells were obtained as described above. Lymphoblastoid cell lines were isolated from cultures of Epstein-Barr virus transformed B cells using standard techniques.

Monoclonal Antibodies. mAb to CD2 (anti-Leu 5b), CD3 (anti-Leu 4, OKT3), CD4 (anti-Leu 3a), CD8 (anti-Leu 2a), CD14 (anti-Leu M3), and HLA-DR (CA141) were produced and purified by standard procedures. mAb directed against CD16 (anti-Leu 11c), anti-Leu 19, anti-$\alpha/\beta$ TCR (WT31) were purchased from Becton Dickinson, Mountain View, Calif. Anti-$\alpha/\delta$ TCR mAb (TCR-$\alpha/\delta$-1) was purchased from T Cell Sciences, Cambridge, Mass. Other mAb used in this study included W6/32 which recognizes a framework determinant on HLA-A, B, C molecules (kindly provided by. Dr. Peter Parham of Stanford university), CD11a (anti-LFA-1$\alpha$, clone TS1/22), CD18 (anti-LFA-1$\beta$), and LFA-3 (clone TS2/9), generous gifts from Dr. Alan Krensky of Stanford University. Antibodies were used as purified unconjugated reagents, or as conjugates to fluorescein isothiocyanate (FITC), biotin or $\beta$-phycoerythrin, prepared as previously described (Sasaki et al).

Culture Medium. Iscove's modified DMEM (Gibco, Grand Island, N.Y.) supplemented with 10% fetal calf serum (FCS), 2 mM L-glutamine, 100 U/ml penicillin, and 100 $\mu$g/ml streptomycin was used as culture medium (CM).

EXAMPLES

Example 1 Cytotoxic activity against 3 different Endothelial cell lines by monocyte-depleted PBL and EC-adherent lymphocytes.

Human microvascular EC lines were derived from preputial skin of randomly selected anonymous newborns and propagated in culture for 5-6 passages as previously described (Bender et al). Microvascular endothelial cell (EC) lines used in functional studies contained less than 1% contaminating cell types, as judged by morphological and ultrastructural criteria (Bender et al). Peripheral blood lymphocytes (PBL) were obtained from a healthy adult volunteer by Ficoll-Hypaque TM gradient separation and monocyte depleted by adherence to plastic and subsequent passage over nylon wool columns. After overnight incubation in medium containing 20 U/ml rIL2 (Cetus Corp.), the PBL preparation was added to confluent EC monolayers in 75 cm$^2$ Falcon TM flasks and allowed to bind for 90 min at 37° C. The nonadherent lymphocytes were then removed by repeated monolayer washing and adherent lymphocytes were recovered by 1% EDTA treatment as previously described (Bender et al). Recovered adherent lymphocytes were utilized as effectors in 4 hr $^{51}$Cr release assays using the following as labeled EC targets: (i) EC cells from the same EC line used for the initial selection and (ii) EC cells from two irrelevant EC lines. Percent $^{51}$Cr release (percent specific cytotoxicity) was determined by the formula: 100×[experimental cpm−spontaneous cpm/maximum cpm−spontaneous cpm]. Maximum cpm was determined by Triton X-100 lysis of labeled target cells. Average spontaneous release by endothelial cells never exceeded 20% of maximum release. Effector to target ratio was 25:1. The results representative of four separate experiments are shown in FIG. 1.

Example 2. Northern blot analysis of an NK (CD3−) cell line (AL45) and the syngeneic T cell (CD3+, CD8+) line (AT45).

A. Preparation of cell lines

PBL's were isolated by Ficoll-Hypaque TM gradient centrifugation, monocyte-depletion, and EC-adhesion as described in the Example 1. CD16+ cells were positively selected using a panning technique (Wysocki et al) with the anti-Leu 11c mAb (clone B73.1, IgG$_1$, which recognizes the Fc receptor on NK cells and granulocytes: Perussia et al, 1984). CD16+ cells were further T cell depleted by sorting the negative population after treatment with a mixture of anti-Leu 4 (anti-CD3, IgG$_1$) and WT31 (anti-TCR, IgG$_1$) antibodies, plus FITC-conjugated goat anti-mouse IgG as a second step. The resultant CD16+ population was less than 0.1% contaminated by CD3−TCR+ cells. A control T cell population was obtained by panning CD16−cells with anti-Leu 3a antibody (anti-CD4, IgG$_1$) and recovery of the negatively selected cells, which were less than 1% CD16+ and 85-95% CD8+. The CD16+ and control T cell populations were co-cultured with confluent EC monolayers in 75 cm$^2$ flasks in the presence of culture medium containing 10% pooled human serum, 150 U/ml recombinant IL2 and 20% conditioned medium—which contains the supernatant derived from normal T-cells stimulated for 48 hours with multiple allogenar LCL and phytohemagglutinin (Mohagheghpour et al). Cultures were re-fed every 4 to 6 days with the same culture medium. After the 3 week culture period, the lymphocytes, which in the case of the CD16+ population were mostly EC-adherent, were recovered with 1% EDTA, terminating the recovery before the ECs detached.

B. Northern blot hybridization Total cellular RNA was isolated from each cell line by lysis in 5M guanidine monothiocyanate, followed by direct RNA precipitation with 4M LiCl (Cathala et al). Poly-A(+) RNA was selected by one cycle of oligo (dT)-cellulose chromatography (Maniatis et al). 2.5 μg of total RNA per lane and 2 μg of poly-A(+) RNA per lane were electrophoresed in 1.2% agarose gel containing 2.2M formaldehyde and blotted onto nitrocellulose filter. After baking for 2 h at 80° C. in vacuo, filters were hybridized to random-primed DNA probes at 42° C. in 50% formamide, 5×SSC (Maniatis et al), 5×Denhardt (Maniatis et al), 50 mM sodium phosphate, pH 7.0, 50 μg/ml salmon sperm DNA. The filters were then washed three times at 50° C. with 0.2×SSC and 0.1% SDS. Panels A and B of FIG. 2 represent results obtained with a TCR-$\beta$ chain specific probe and a TCR-$\gamma$ chain specific probe, respectively: lane 1, poly-A(+) RNA from B cells; lane 2, total RNA, B cells; lane 3, total RNA, NK (CD3−) cell line; lane 4, total RNA, syngeneic T cell (CD3+, CD8+); lane 5, total RNA, PEER; lane 6, poly-A(+) RNA, HPB-ALL.

Example 3 Cytotoxic activity of three selected natural killer cell lines generated by continuous stimulation with EC lines.

Three cytotoxically active natural killer (NK) cell lines (AL45, AL158, and AL178) were generated by continuous stimulation with EC lines 45, 158, and 178 by the methods described in Example 1. The starting cells for AL158 and AL178 were derived from the same individual.

Panels a, b, c of FIG. 3 show the cytotoxicity of the NK cells against the EC lines used in the sensitization cultures (a: EC45; b: EC158; c: EC178) and several unrelated EC lines. Panels d, e, f of FIG. 3 show the cytotoxicity of the NK cells (E/T ratio 1:1) against allogeneic Epstein-Barr virus transformed lymphoblasts, skin fibroblasts syngeneic to the EC lines used as stimulators (d: Fibr.45; f: Fibr.178) or derived from a genetically unrelated individual (f: Fibr.57SK). Specific cytotoxicity was evaluated in a 4 hr assay using $^{51}$Cr-labeled targets as described in Example 1.

Example 4 Generation of natural killer cell lines specific for allogenic lymphoblastoid cell lines Peripheral blood lymphocytes from healthy normal volunteers were isolated by Ficoll-Hypaque ™ gradient centrifugation, and monocytes and B cells were removed by passage over nylon wool columns. To obtain CD3−, CD5− cells, cells devoid of monocytes and B cells were incubated with anti-CD3 mAb and applied to plastic petri dishes precoated with goat anti-mouse Ig (panning) as described (Engleman et al). This procedure was repeated twice, and then the nonadherent cells were incubated with anti-CD5 mAb and panned on anti-mouse Ig to remove any residual CD5+ cells. The resultant lymphocyte population contained 0.5% CD3+ cells and 85% Leu 11c+ (CD16) cells by flow cytometric analysis; greater than 85% of these cells were also leu19+.

To generate NK lines and clones, purified CD3−, CD16+ cells were incubated at 37° C. for one hour on a monolayer of irradiated (10,000 rads) lymphoblastoid cells which had been bound to flat-bottomed microtiter wells with CELL-TAK ™ (BioPolymers, Inc., Farmington, Conn.). Thereafter, cells not adherent to the lymphoblastoid cell lines (LCLs) were washed out and adherent cells were cultured in medium supplemented with IL2-containing supernatant (Fathman et al) at 37° C. in 5% $CO_2$/air. After being cultured for one week the growing cells were isolated on Ficoll-Hypaque ™ gradients, and maintained as bulk cultures in 48-well plates, or cloned at 0.7 cells/well in 96 microwells. Culture medium (CM) supplemented with IL2 containing supernatant was added every 2–3 days, and $1 \times 10^5$ irradiated original LCL were also added weekly to each well. With this procedure multiple NK lines and clones were obtained and maintained for more than 6 months.

FIG. 4 shows the results of two-color flow cytometric analysis of cell surface antigens on a cell line derived from fresh CD3−, CD16+ lymphocytes. After 6 weeks of continuous expansion in the presence of irradiated LCL feeders, a representative cell line was separated from feeder cells over a Ficoll-Hypaque gradient and analyzed by two-color immunofluorescence in an Ortho System 50H cell sorter. The same staining pattern has been obtained repeatedly over a 6 month period of continued propagation of this line.

Example 5 Message amplification phenotyping of an NK cell line.

To analyze mRNA transcripts in NK lines and clones, some of which were available in numbers less than 10⁷, we utilized a method based on detection of amplified cDNA (Brenner et al). A microadapted guanidinium thiocyanate/cesium chloride procedure was used to prepare total RNA from NK cells (Brenner et al). 1×10cells were added to 100 μl of guanidinium thiocyanate solution and then layered over 100 μl of 5.7M cesium chloride solution and centrifuged for $20 \times 10^6$ g. min/cm gradient. The pelleted RNA was resuspended, and ethanol precipitated (Brenner et al). First strand DNA was synthesized for 1 hr in a 10 μl reaction volume with oligo-dT primer. Five μl of this reaction mixture contains 16 U Moloney murine leukemia virus reverse transcriptase (BoehringerMannheim, Chicago, Ill.), 5 U RNAsin (Promega, Madison, Wis.), 0.2 g oligo-dT primer, $1 \times 10^{-2}$ μM dithiothreitol and $1 \times 10^{-2}$ μM dNTP mix (Pharmacia, Piscataway, N.J.) (Brenner et al). To amplify these first strand cDNAs with the polymerase chain reaction (PCR), Thermus aquaticus thermostable DNA polymerase (Cetus-Perkin Elmer, Emeryville, Calif.) was used according to the manufacturer's protocol.

Oligonucleotide PCR primers were designed using published or GENEBANK sequences. Sequences within the coding regions for the 5' primers and 3' primers were as follows: Beta actin:

5' primer, GGGAATTCATGGATGAT-GATATCGCCGCG;

3' primer, GGAAGCTTCTAGAAG-CATTTGCGGTGGACGATGGAGGGGCC;

TCR alpha constant region:

5' primer, GGGAATTCAATATCCAGAACCCT-GACCCTGCCGTGTAC;

3' primer, GGAAGCTTGCTGGACCACAGCC-GCAGCGTCATGAGCAG; TCR beta constant region:

5' primer, GGGAATTCGTCGCTGTGTT-GAGCCATCAGAAGCAGAG;

3' primer, GGAAGCTTATCCTTTCTCTTGAC-CATGGCCAT; TCR gamma constant region:

5' primer, GGGAATTCTGAGCACTAGATTTG-CTACAAACCAGCATC;

3' primer, GGAAGCTTAAATGCAATAGAGG-CAGAGGCTGAGAAG; TCR delta constant region:

5' primer, GGGAATT-CACATACCTTTGTCTTCTT-GAGAAATTTTC;

3' primer, GGAAGCTTTTATGATTTCTCT-CCATTGCAGCAGAAAGC; CD3 gamma chain:

5' primer, GGGAATTCGG-GGAAGGGCCTGGCTGTCCT-CATCCTGGCT;

3' primer, GGAAGCTTCTCTCGACTGG-CGAACTCCA; CD3 delta chain:

5' primer, GGGAATTCTAG-CACGTTTCTCTCTGGCTTGGTACTGGCT;

3' primer, GGAAGCTTCCCCAGACAGCCTT-CCAGTC; CD3 epsilon chain:

5' primer, GGGAATTCTGCCCTCAGTATCCT-GGATCTGAAA;

5' primer, GGAAGCTTCTAGCCCAG-GAAACAGGGACTCGCAGGGGG.

These primers were designed to yield PCR fragments of approximately 500 bases. Fidelity of the amplified sequences was confirmed by directly sequencing the fragments or by Southern blotting using cDNAs or probes contained within the PCR fragments. Oligonucleotides were synthesized on an Applied Biosystems 380B DNA synthesizer (Foster City, Calif.) and purified by C18 reverse phase HPLC (Rainin Instruments, Emeryville, Calif.). The reaction mixture was subjected to PCR amplification using a Perkin-Elmer thermal cycler set for 20-35 cycles depending upon the experiment. The temperatures used for PCR were: Melt 94° C., 1 min; primer anneal 55° C., 2 min; primer extension 72° C., 3 min. The PCR fragments were separated on 2% agarose gels and detected by ethidium bromide staining (Brenner et al).

Messenger RNA from LCL ND, T cell leukemia cells Jurkat and PEER, and the NK-D line were reverse transcribed, amplified using the PCR technique, and the amplified PCR fragments were analyzed on 2% agarose gels. The results of the amplifications are shown in FIGS. 5A-B:

Panel A—Lanes 1 and 18, 1 kb ladder (Bethesda Research Laboratory); lanes 2-4 the primers were for TCR$\alpha$ constant region, 2:LCL, 3:Jurkat, and 4:NK-D line; lanes 5-7 the primers were for TCR$\beta$ constant region, 5:LCL, 6:Jurkat, and 7:NK-D line; lanes 8-10 the primers were for TCR$\gamma$ constant region, 8:LCL, 9:PEER, and 10:NK-D line; lanes 11-13 the primers were for TCR$\delta$ constant region, 11:LCL, 12:PEER, and 13:NK-D line; lanes 14-17, the primers were for actin, 14:LCL, 15:Jurkat, 16:PEER, and 17:NK-D line.

Panel B—Lanes 1 and 11, 1 kb ladder; lanes 2-4 the primers were for CD3 gamma chain, 2:LCL, 3:Jurkat, and 4:NK-D line; lanes 5-7 the primers were for CD3 delta chain, 5:LCL, 6:Jurkat, and 7:NK-D line; lanes 8-10 the primers were for CD3 epsilon chain, 8:LCL, 9:Jurkat, and 10:NK-D line.

Example 6 Immunofluorescence Analysis of LCL stimulated NK cell lines.

NK lines and clones were analyzed by immunofluorescence on an Ortho System 50H Cytofluorograf for the expression of a variety of cell surface antigens. Some antibodies were available as direct fluorochrome conjugates and were used as direct staining reagents, whereas other (biotinylated) antibodies were used in combination with avidin-phycoerythrin for indirect immunofluorescence analysis as previously described (Sasaki et al).

The results of the flow cytometric analysis are shown above in Table 3.

Example 7 Cytotoxic activity of LCL stimulated NK cell lines and clones.

A. Target Cells.

The following cultured cell lines were used as targets in cytotoxicity assays:

K562, a proerythroblastic cell line isolated from a patient with chronic myelogenous leukemia;

LCLs:
ARENT (HLA-A2, 2; B38, 39; DR6, 6),
SKF (HLA-A24, 30; B18, w35; DR5, 5),
MSAB (HLA-A1, 2; B57, 57; DR7, 7),
ND (HLA-A26, 29; B7, 55; DR9, 10), and
JEK (HLA-A2, 11; B39, 62; DR4,-). None of the LCLs had detectable surface Ig on the basis of immunofluorescent staining (data not shown).

B. Cytotoxicity Assays.

NK cell lines and clones were tested for cytotoxicity in 4 hour 51chromium (Cr)-release assays as described (Takada et al). Briefly, varying numbers of effectors were mixed with $2.5 \times 10^3$ $^{51}$Cr-labeled target cells from either the original stimulator line, irrelevant LCLs or K562 cells in 96-well round-bottom plates. (Costar, Cambridge, Mass.). The plates were centrifuged for 5 minutes and then incubated for 4 hours at 37° C. Samples were harvested with a Skatron harvester (Lier, Norway) and counted in a gamma counter. In experiments designed to explore the role of cell surface molecules in cytotoxicity, mAbs were introduced and were present during the 4 h $^{51}$Cr-release assays. Assays were performed in triplicate and the results, given in FIG. 6, are presented as the percent $^{51}$Cr-released. These $^{51}$Cr-release values were calculated by the following formula: cytotoxicity = 100×(experimental release (cpm)-spontaneous release (cpm))/(maximum release (cpm)-spontaneous release (cpm)), where spontaneous release represents the amount of $^{51}$Cr released by target cells in the absence of effectors, and maximum release represents the amount of $^{51}$Cr released by target cells treated with 0.7% Triton detergent.

Lines and clones generated as described in the text were tested for cytotoxic activity against the original stimulator LCL, irrelevant LCLs, and K562 cells, using a standard $^{51}$Cr-release assay as described above. The values in FIG. 6 represent the mean percent killing of triplicate assays. The original stimulators for each line and clone are indicated in parentheses.

C. Cold Target Inhibition Assays.

Target cells were labeled with $^{51}$Cr as above and dispensed into 96-well plates at $2.5 \times 10^3$ cells/well. Unlabeled (cold) target cells were added to the wells at unlabeled/labeled target cell ratios ranging from 0:1 to 100:1. Effector cells were then added at various effector/labeled target cell ratios, and the plates were incubated at 37° C. for a 4 hour $^{51}$Cr-release assay. The percent $^{51}$Cr-release was calculated as above.

Effects of unlabeled (cold) target cells on the cytolytic activity of a CD3− line and a CD3− clone are shown in FIGS. 7A–D. Unlabeled target cells (K562, specific stimulator LCL ARENT, or irrelevant LCLs) were tested for their ability to inhibit the lysis of $^{51}$Cr-labeled K562 cells (panels A for line D and panel C for clone-3) or specific stimulator LCL ARENT (panel B for the line and panel D for the clone). An effector to $^{51}$Cr-labeled target ratio of 12:1 for B, C and D and 24:1 for A was maintained in all assays, as increasing numbers of cold inhibitor cells were added.

Example 8 Effects of various mAbs on the cytolytic activity of a CD3-cell line and a CD3-clone.

The NK cell line B and clone A were tested for cytotoxicity against the original stimulator LCL ARENT (panel A, FIG. 8, for the effector line and panel C for the effector clone) or K562 cells (panel B, FIG. 8, for the line and panel D, FIG. 8, for the clone) in the presence or absence of anti-HLA class I (W6/32, 25 μg/ml), anti-HLA-DR (CA141, 25 μg/ml), anti-CD3 (OKT3, 25 μg/ml), anti-CD11a (LFA-1α, 1:10), anti-CD18 (LFA-1β, 1:10), anti-LFA-3 (1:10), anti-CD2 (Leu 5b, 25 μg/ml) or anti-CD14 (Leu M3, 1:10). Effector:target ratio was 20:1 in panels A and B, and 5:1 in panels C and D. Values represent the mean percent killing ± SE (standard error) of triplicate assays.

While the invention has been described with respect to specific embodiments, methods and applications, it will be recognized by those skilled in the art that modifications of the composition and methods of the invention involving target-specific natural killer cells may be made without departing from the spirit and scope of the present invention.

What is claimed is:

1. A method of preparing natural killer cells, comprising
    obtaining a partially purified preparation of natural killer cells,
    contacting said preparation with a selected target cell type,
    selecting natural killer cells based on their adhesion to the selected target cell type, and
    culturing the selected natural killer cells by providing an agent which promotes proliferation of the selected natural killer cells, where the proliferated NK cells demonstrate preferential cytotoxicity against the target cell type to which they originally adhered.

2. The method of claim 1, where said partial purification includes removing the monocytes, B-cells, CD3+ and CD5+ cells.

3. The method of claim 2, where said removing includes passing the peripheral blood lymphocytes over nylon wool columns followed by incubation of the remaining lymphocytes in the presence of anti-CD3 and anti-CD5 monoclonal antibodies.

4. The method of claim 3, wherein the partially purified natural killer cells are less than about 0.5% CD3+ cells and greater than about 85% CD16+ cells.

5. The method of claim 3, wherein the partially purified natural killer cells are less than about 0.5% CD3+ cells and greater than about 85% leu19+ cells.

6. The method of claim 1, wherein said contacting includes incubating the partially purified natural killer cells in the presence of a monolayer of the selected target cell type and washing away the natural killer cells that have not adhered to the target cells.

7. The method of claim 1, wherein said culturing of the enriched natural killer cells is performed with the addition of interleukin-2 to the culture medium.

8. A preparation of natural killer cells prepared essentially as follows:
    obtaining a partially purified preparation of natural killer cells,
    contacting said preparation with a selected target cell type,
    selecting natural killer cells based on their adhesion to the selected target cell type, and
    culturing the selected natural killer cells by providing an agent which promotes proliferation of the selected natural killer cells, where the proliferated NK cells demonstrate preferential cytotoxicity against the target cell type to which they originally adhered.

9. The preparation of claim 8 which contains less than about 0.5% CD3+ cells and greater than about 85% CD16+ cells.

10. The preparation of claim 8 which contains less than about 0.5% CD3+ cells and greater than about 85% leu19+ cells.

11. The preparation of claim 8, wherein the selected target cell type is either microvascular endothelium or a lymphoblastoid cell line.

12. The preparation of claim 8, wherein the selected target cell type is selected from the group consisting of tumor cells and virus-infected cells.

13. The preparation of claim 8, wherein said contacting includes incubating the partially purified natural killer cells in the presence of a monolayer of the selected target cell type and washing away the natural killer cells that have not adhered to the target cells.

14. The preparation of claim 8, wherein said culturing of the enriched natural killer cells is performed with the addition of interleukin-2 to the culture medium.

* * * * *